United States Patent [19]

Shieh et al.

[11] Patent Number: 5,428,159
[45] Date of Patent: Jun. 27, 1995

[54] METHOD OF MANUFACTURE OF (−)-GALANTHAMINE IN HIGH YIELD AND PURITY SUBSTANTIALLY FREE OF EPIGALANTHAMINE

[75] Inventors: Wen-Chung Shieh; John A. Carlson, both of Berkeley Heights, N.J.

[73] Assignee: Ciba-Geigy Corporation, Ardsley, N.Y.

[21] Appl. No.: 224,932

[22] Filed: Apr. 8, 1994

[51] Int. Cl.$^6$ .......................................... C07D 491/08
[52] U.S. Cl. .................................................... 540/581
[58] Field of Search ........................................ 540/581

[56] References Cited

PUBLICATIONS

Barton et al, J. Chem. Soc. 1962, 806–817. "Phenol Oxidation and Biosynthesis. Part V. The Synthesis of Galanthamine".
Shimizu et al, Heterocycles 1977, 8, 277–282. "A Biogenetic-Type Asymmetric Synthesis of Optically Active Amaryllidaceae Alkaloids . . . ".
Shimizu et al, Chem. Pharm. Bull. 1978, 26, 3765–3771. "Stereochemical Studies. LIV. A Biogenetic-Type Asymmetric Synthesis of Optically Active Galanthamine from L-Tyrosine".
Szewczyk et al, J. Heterocycl. Chem 1988, 25, 1809–1811 "An Improved Synthesis of Galanthamine".
Kametani et al, J. Org. Chem. 1971, 36, 1295–1297 "Studies on the Synthesis of Heterocyclic Compounds. CCCXCVI. An Alternative Total Synthesis of (±)-Galanthamine."
Kametani et al, J. Chem. Soc. Perkin Trans. 1, 1972, 1513 "Studies on the Synthesis of Heterocyclic Compounds. Part CDLXVI. Synthesis of Narwedine Type Enones By Photochemical Cyclisation."
Kametani et al, J. Heterocycl. Chem. 1973, 10, 35 "Studies on the Synthesis of Heterocyclic Compounds. Part DVII(1) A Synthesis of (±)-N-Norgalanthamine."
Vlahov et al, Tetrahedron 1989, 45, 3329 "Synthesis of Galanthamine and Related Alkaloids—New Approaches. I.".
Holton et al, J. Am. Chem. Soc. 1988, 110, 314–316 "Palladium-Mediated Biomimetic Synthesis of Narwedine".

*Primary Examiner*—John M. Ford
*Attorney, Agent, or Firm*—Irving M. Fishman; Karen G. Kaiser

[57] ABSTRACT

(−)-Galanthamine is obtained in substantially high yield and purity substantially without concomitant production of epigalanthamine by conversion of racemic narwedine to (−)-narwedine and subsequent reduction to (−)-galanthamine using bulky organo-aluminum or organo-boron reducing agents.

20 Claims, No Drawings

METHOD OF MANUFACTURE OF (−)-GALANTHAMINE IN HIGH YIELD AND PURITY SUBSTANTIALLY FREE OF EPIGALANTHAMINE

FIELD OF THE INVENTION

The invention relates to manufacturing processes of pharmaceutically active alkaloids. In particular it relates to obtaining active enantiomers of natural alkaloids without having to extract and separate the enantiomers from natural sources. The invention further relates to the natural alkaloid galanthamine and obtaining the active enantiomer thereof from racemic precursors. It further relates to obtaining enantiomeric galanthamine derivatives, especially ethers, esters and amides.

BACKGROUND OF THE INVENTION (−)-Galanthamine is a tertiary Amaryllidaceae alkaloid having acetylcholinesterase inhibitor properties thereby enhancing cholinergic function. The cholinesterase inhibitors have recently been under investigation for use as nootropics, in particular, in the treatment of Alzheimer's disease. Currently, galanthamine is only available through an extraction from daffodils (Narcissus Pseudonarcissus L.). The extraction process has proved to be quite expensive for pharmaceutical grade material, even when taking into account large scale production efficiencies.

An alternate source of (−)-galanthamine is its chemical synthesis. Some synthetic routes to galanthamine have been published over the last 30 years, beginning with the work of Barton and Kirby in 1962 (J. Chem. Soc. 1962, 806). Over the years, other contributors to synthetic steps in the production of galanthamine from readily available materials have included Shimizu et at, Heterocycles 1977, 8, 277; and Shimizu et at, Chem. Pharm. Bull. 1978, 26, 3765. Additional contributions to the production of racemic galanthamine (which would still need to be resolved) have: been made by Szewczyk et at, J. Heterocycl. Chem., 1988, 25, 1809; Karnetani et at, J. Org. Chem. 1971, 36, 1295; Kametani et al, J. Chem. Soc. Perkin Trans. 1, 1972, 1513; Kametani et al, J. Heterocycl. Chem. 1973, 10, 35; Vlahov et al, Tetrahedron 1989, 45, 3329; and Holton et al, J. Am. Chem. Soc. 1988, 110, 314. Holton's work provided a short and elegant synthesis of racemic narwedine; (−)-narwedine is the biogenic precursor of (−)-galanthamine. Notwithstanding these advances, the synthetic approach to (−)-galanthamine production in high purity pharmaceutical grade on a commercial scale is still problematical.

In 1962 Barton et al reported the first successful chemical synthesis of (−)-galanthamine by reducing (−)-narwedine, which itself was obtained by chemical resolution on a small laboratory scale. Barton's process was able to yield racemic narwedine in an amount of about 1.4%. Banon then reduced the racemic narwedine with lithium aluminum hydride and obtained both racemic galanthamine and racemic epigalanthamine. Banon further reported that the Ponndorf-Meerwein reduction of racemic narwedine gave mostly racemic epigalanthamine. In the course of oxidizing (−)-galanthamine (obtained from extraction or other sources) to narwedine (to confirm structures), Banon found that the presence of some unoxidized (−)-galanthamine remaining in the oxidation product mixture resulted in (+)-narwedine, rather than racemic narwedine. Reduction of this gave (+)-galanthamine and (+):epigalanthamine. These were then used as is to resolve racemic narwedine to obtain the (−) compound. On obtaining the (−)-narwedine, Banon then reduced the material to obtain a mixture of (−)-galanthamine and (−)-epigalanthamine. Typically, the reduction reported by Barton resulted in about 40% of the yield being epigalanthamine.

According to Banon, the greater the amount of enantiomeric galanthamine used, the better the resolution of narwedine. Basically, the Banon process took racemic narwedine and used some (−)-galanthamine to produce (+)-narwedine. This was then reduced to the (+)-galanthamine and (+)-epigalanthamine, which were then used to convert additional racemic narwedine to (−)-narwedine, which would be reduced to (−)-galanthamine and (−)-epigalanthamine. Clearly, this was an extremely wasteful process and not very suitable to large scale production.

At page 810 of the Banon et al article, the authors report that the standard resolution techniques were not successful, whether applied to narwedine or galanthamine, therefore making the above complicated process necessary to achieve (−)-galanthamine through synthetic means.

Szewczyk et at, in J. Heterocyclic Chem. 25, 1809 (1988), disclose an alternate process which goes through a narwedine analog yielding about 50% racemic galanthamine and about 30% racemic epigalanthamine. Kametani et al, J. Org. Chem. 36, No. 9, 1971, 1295–1297, also report still another synthesis. Both of these references utilize lithium aluminumhydride as the reducing agent to reduce the precursor to galanthamine. In each case, racemic material is obtained as a mixture of both galanthamine-and epigalanthamine. The two Shimizu et al articles relate; complex synthetic mutes to enantiomeric galanthamine (not really related to the present processes) in fairly low overall yield.

As mentioned above, Holton et al reported a short, elegant synthesis of racemic narwedine in 1988.

Notwithstanding all of these researchers attempting to find an economic, scalable, synthetic route for (−)-galanthamine, none has been adequately found. Either the processes are so involved as to make the overall yields totally unacceptable or too expensive, or the processes end in the need to resolve the racemates or in the inefficient concomitant production of substantial amounts of epigalanthamine.

OBJECTS OF THE INVENTION

It is therefore an object of the invention to provide a means to convert (−)-narwedine to (−)-galanthamine with substantially less, essentially no, simultaneous production of epigalanthamine.

It is another object of the invention to provide an efficient process for the conversion of racemic narwedine into (−)-narwedine for further conversion to (−)-galanthamine.

A further object of the invention is the synthetic production of enantiomeric ethers, esters, or amides of galanthamine and/or narwedine.

SUMMARY OF THE INVENTION

The foregoing objects, and others, are obtained by the present invention, which is a process for the manufacture of enantiomeric galanthamine (or its ethers, esters, or amides or analogs thereof) of formula I or formula Ia comprising reacting enantiomeric narwedine (or its corresponding ethers, esters, or amides or analogs thereof) of formula II or formula IIa with a reducing agent selected front the group consisting of compounds of formulas III-VII:
wherein formulas I-VII are:

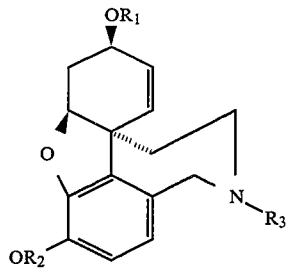 (I)

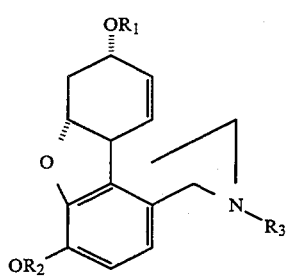 (Ia)

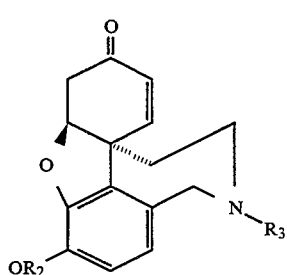 (II)

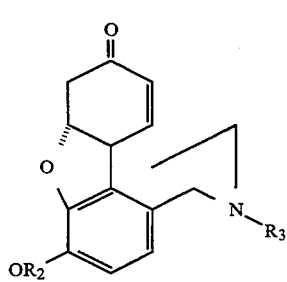 (IIa)

$MB(R_4)_pH_{4-p}$;  (III)

$M_qAl(R_4)_mH_{(3+q)-m}$;  (IV)

$MAl(OR_5)_nH_{4-n}$;  (V)

$NaBH_4/CeCl_3$;  (VI)

$LiAlH_4/AlCl_3$; and  (VII)

mixtures thereof; in which $R_1$ and $R_2$ are independently selected from (a) hydrogen; (b) $C_{1-7}$ straight or branched alkyl, preferably straight or branched $C_{1-4}$alkyl, most preferably methyl of ethyl; (c) straight or branched $C_{1-7}$ alkanoyl, preferably straight or branched $C_{1-4}$alkanoyl, most preferably acetyl; and (d) $(R_6)(R_7)N-C(O)-$ in which each of $R_6$ and $R_7$ is selected from hydrogen or straight or branched $C_{1-7}$alkyl, preferably straight or branched $C_{1-4}$alkyl, most preferably methyl or ethyl, or one of $R_6$ and $R_7$ may also be phenyl, and in any event preferably one of $R_6$ and $R_7$ is other than hydrogen; $R_3$ is selected from the groups (a)-(c) defined for $R_1$ above; m is 1, 2, or 3; n is 1, 2, or 3; p is 1, 2, or 3; q is 0 or 1; M is Li, Na, or K; each $R_4$ is independently selected from the group consisting of straight and branched alkyl having 2-7 carbon atoms; and each $R_5$ is independently selected from the group consisting of straight and branched alkyl having 2-7 carbon atoms and $R_8-O-R_9-$ in which each $R_8$ is independently straight or branched alkyl of 1-3 carbon atoms, and each $R_9$ is independently 1,2-$C_{2-3}$alkylene or 1,3-propylene;

whereby said (−)-galanthamine (or its corresponding ether or ester or amide) is produced without more than 20% production of epigaianthamine (or its corresponding ether or ester or amide ).

DETAILED DESCRIPTION OF THE DISCLOSURE

The present invention is ultimately a process for the production of (−)-galanthamine (or its ethers, esters, or amides) from (−)-narwedine (or its ethers, esters, or amides) which is free from the problems associated with the art processes which attempt a similar conversion. These art processes had significant losses in yield or had substantial amounts diverted to side reactions such that substantial losses resulted. In particular, much of the art had problems with epigaianthamine, being produced. The present invention results in very much lower amounts of epigalanthamine (or its ethers, esters, or amides) being produced; in fact, substantially no epigalanthamine (or its ethers, esters, or amides) results from the invention process.

The present invention is a process for the manufacture of (−)-galanthamine (or its ethers, esters, or amides) of formula I comprising reacting (−)-narwedine (or its ethers, esters, or amides) of formula II with a reducing agent selected from the group consisting of compounds of formulas III-VII, where in formulae I-VII are:

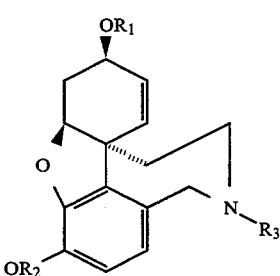 (I)

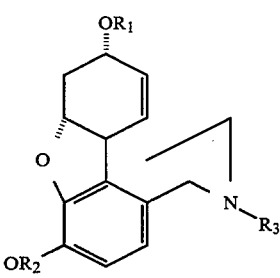 (Ia)

-continued

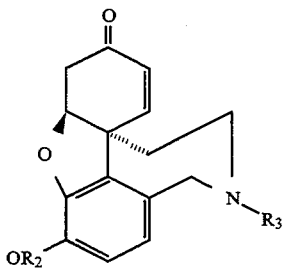
(II)

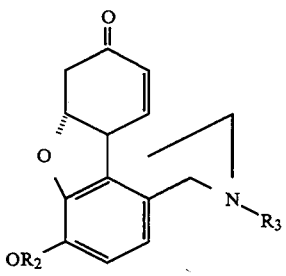
(IIa)

MB(R$_4$)$_p$H$_{4-p}$; (III)

M$_q$Al(R$_4$)$_m$H$_{(3+q)-m}$; (IV)

MAl(OR$_5$)$_n$H$_{4-n}$; (V)

NaBH$_4$/CeCl$_3$; (VI)

LiAlH$_4$/AlCl$_3$; and (VII)

mixtures thereof; in which R$_1$ and R$_2$ are independently selected from (a) hydrogen; (b) C$_{1-7}$ straight or branched alkyl, preferably straight or branched C$_{1-4}$alkyl, most preferably methyl of ethyl; (c) straight or branched C$_{1-7}$alkanoyl, preferably straight or branched C$_{1-4}$alkanoyl, most preferably acetyl; and (d) (R$_6$)(R$_7$)N—C(O)— in which each of R$_6$ and R$_7$ is selected from hydrogen or straight or branched C$_{1-7}$alkyl, preferably straight or branched C$_{1-4}$alkyl, most preferably methyl or ethyl, or one of R$_6$ and R$_7$ may also be phenyl, and in any event preferably one of R$_6$ and R$_7$ is other than hydrogen; R$_3$ is selected from the groups (a)–(c) defined for R$_1$ above; m is 1, 2, or 3; n is 1, 2, or 3; p is 1, 2, or 3; q is 0 or 1; M is Li, Na, or K; each R$_4$ is independently selected from the group consisting of straight and branched alkyl having 2–7 carbon atoms; and each R$_5$ is independently is selected from the group consisting of straight and branched alkyl having 2–7 carbon atoms and R$_8$—O—R$_9$— in which each R$_8$ is independently straight or branched alkyl of 1–3 carbon atoms, and each R$_9$ is independently 1,2-C$_{2-3}$alkylene or 1,3-propylene; whereby said (−)-galanthamine (or its ethers, esters, or amides) is produced without more than 20% production of epigaianthamine (or its ethers, esters, or amides) of formula VIII

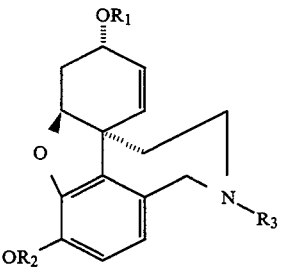
(VIII)

in which R$_1$–R$_3$ are as defined above. If the other enandomers of galanthamine (or its ethers, esters, or amides) of formula Ia are desired, the process merely employs the narwedine (or its ethers, esters, or amides) enantiomer of formula IIa, and the product is produced with the lower amounts of the epigalanthamine (or its ethers, esters, or amides) enantiomer of formula VIIIa

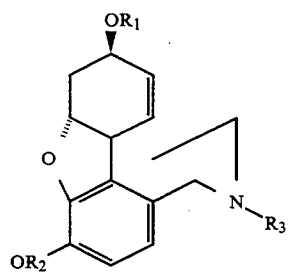
(VIIIa)

in which R$_1$–R$_3$ are as defined above.

As stated above, racemic narwedine is well known in the art and is conveniently made from other materials in the process set forth by Holton et al., J. Am. Chem. Soc. 110, 314–316, 1988. Whether one's synthesis has R$_2$ and/or R$_3$ corresponding to narwedine and galanthamine or some other group within the definitions of R$_2$ and R$_3$ above, these may be altered by processes in the art before resolution of the formula II/IIa racemate; after the resolution thereof but before the reduction step; or after achieving the compound of formula I or Ia. The R$_1$ group may be changed only after a compound of formula I or Ia is obtained.

The resolution of the racemate is carried out with either seeds of (−)-narwedine or (+)-galanthamine or one of their esters, ethers, or amides if (−)-narwedine (or one of its ethers, esters, or amides) is the desired enantiomer. (+)-narwedine or (−)-galanthamine or one of their esters, ethers, or amides are used if (+)-narwedine (or one of its ethers, esters, or amides) is the desired enantiomer. It is most preferable for the R$_2$ and R$_3$ groups to be the same in the resolving agent (a formula I, formula Ia, formula II, or formula IIa compound) as will be present in the formula II/IIa racemate being resolved, but this is not critical.

If needed, an initial crop of (−)-galanthamine (obtained from natural product extraction or other sources) or one of its ethers, esters, or amides can be used to obtain the (+)-narwedine (or one of its ethers, esters, or amides), which can then be reduced by the procedures here to (+)-galanthamine (or one of its ethers, esters, or amides depending on the narwedine derivative used). This product can then be used to initially crystallize out the (−)-narwedine (or one of its ethers, esters, or amides) from racemic narwedine (or from a racemate of one of its ethers, esters,, or amides). Once this batch of (−)-narwedine (or one of its ethers, esters, or amides) is obtained, the direct use of some (−)-narwedine (or one of its ethers, esters, or amides) from one production batch can be used as seed crystals for the next batch.

The (−)-narwedine (or one of its ethers, esters, or amides) is then reduced using the reducing agents set forth below to surprisingly and unexpectedly give high yields of highly pure (−)-galanthamine (or one of its ethers, esters, or amides) without substantial amounts of epigalanthamine (or one of its ethers, esters, or amides). For the balance of this disclosure wherever galanthamine, narwedine or epigalanthamine are mentioned, they include the ethers, esters, and amides thereof within the definitions of formulae I, Ia, II, IIa, VIII, and VIIIa, unless the text specifies otherwise.

The reducing agents for use in the conversion of enantiomeric narwedine to enantiomeric galanthamine are selected from the group consisting of $MB(R_4)_pH_{4-p}$(III);
$M_qAl(R_4)_mH_{(3+q)-m}$(IV);
$MAl(OR_5)_nH_{4-n}$(V);
$NaBH_4/CeCl_3$(VI);
$LiAlH_4/AlCl_3$(VII); and mixtures thereof; in which m is 1, 2, or 3, preferably 2; n is 1, 2, or 3, preferably 3; p is 1, 2, or 3, preferably 3; q is 0 or 1; M is Li, Na, or K; each $R_4$ is independently selected from the group consisting of straight and branched alkyl having 2–7 carbon atoms, preferably 2–5 carbon atoms, such as methyl, ethyl, n-butyl, sec-butyl, iso-butyl, t-butyl, amyl, iso-amyl, sec-amyl, and t-amyl, most preferably sec-butyl, and isoamyl; and each $R_5$ is independently is selected from the group consisting of straight and branched alkyl having 2–7 carbon atoms, preferably 2–5 carbon atoms, such as methyl, ethyl, n-butyl, sec-butyl, iso-butyl, t-butyl, amyl, iso-amyl, sec-amyl, and t-amyl, most preferably sec-butyl, and isoamyl; and $R_8$—O—$R_9$— in which each $R_8$ is independently straight or branched alkyl of 1–3 carbon atoms, and each $R_9$ is independently 1,2-$C_{2-3}$alkylene or 1,3-propylene. Preferably these reducing agents include, without limitation, bis(2-methoxyethoxy)aluminumhydride; lithium sec-butyl-bis-isobutylaluminumhydride; sodium borohydride/cesium chloride; lithium aluminumhydride/aluminum chloride; lithium tri-sec-butylborohydride; lithium trisisoamylborohydride; potassium tri-sec-butylborohydride; potassium trisisoamylborohydride; sodium tri-sec-butylborohydride; and sodium trisisoamylborohydride.

The reduction reaction is carried out at a temperature of from −100° C. to 25° C., preferably from −90° C. to −20° C., more preferably from −80° C. to −40° C., most preferably at about −78° C., and in a solvent selected from tetrahydofuran, toluene, diethylether, methylene chloride, and dichloroethane, preferably tetrahydrofuran. The resulting crystals are filtered off, washed in any suitable solvent known in the art, preferably heptane, or cyclohexane, and dried for use as is (as the active agent in the case of the (−)-galanthamine or as the further resolution aid in the case of the (+)-galanthamine). While not usually necessary, further crystallization or purification steps known within the art can be utilized to reduce or remove any remaining epigalanthamine.

The resolution reaction from racemic narwedine to enantiomerically pure narwedine is carded out at a temperature from 20° C. to 80° C., preferably 30° C. to 60° C., most preferably about 40° C., in a solvent/amine base mixture in which the solvent is selected from ethanol, isopropanol, toluene, acetone, acetonitrile, tetrahydrofuran, and ethyl acetate, while the amine base is selected from pyridine and $(R_{10})_3N$ in which each $R_{10}$ is independently a $C_{2-4}$alkyl. The ratio of the solvent:base is from 1:9 to 15:1, most preferably about 9:1.

Once dissolved, the racemic narwedine mixture is maintained at a temperature of 25° C. to 70° C., preferably 40° C. to 60° C., and the crystals of enantiomeric narwedine, enantiomeric galanthamine, or enantiomeric epigalanthamine in an amount of from 0.1% to 2%, preferably 0.2% to 1% by weight relative to the amount of narwedine to be resolved are added. If (−)-narwedine is to be produced, the crystals added here are either (−)-narwedine, (+)-galanthamine, or (+)-epigalanthamine. If the reaction is to produce (+)-narwedine, the crystal used here are (+)-narwedine, (−)-galanthamine or (−)-epigalanthamine. Since the end result of the next step (the reduction to (−)-galanthamine) is intended to be as free as possible of epigalanthamine and (+)-galanthamine, (−)-narwedine is the most preferred crystal to use to generate additional (−)-narwedine so long as it is available. The temperature is then dropped to 25° to 70° C., preferably 40° C. to 60° C. and held there for 5–24 hours, preferably 12–18 hours, most preferably about 16 hours.

EXAMPLES

The following Examples are: provided to further exemplify, but do not limit, the invention.

Example I: Resolution of (±)-Narwedine to (+)-Narwedine using (−)-Galanthamine as Resolving Agent 0.5 grams of (±)-narwedine are dissolved into 8 ml of a boiling mixture of 95% ethanol/triethylamine (9:1 ). After dissolution, the mixture is cooled to 70° C. and 1 mg (0.2%) of crystals of (−)-galanthamine are added. The mixture is then cooled to 60° C. and held them for 24 hours. The resulting white suspension is slowly cooled to room temperature and held there for 3 hours. The resulting precipitate is filtered, rinsed with the same solvent mixture and dried to yield 0.37 g of white solid (74%) which is identified as (+)-narwedine {m.p. 192°–193° C.; $[\alpha]_D^{25} = +418$}.

Example II: Resolution of (±)-Narwedine to (+)-Narwedine using (+)-Narwedine as Resolving Agent 0.2 grams of (±)-narwedine is dissolved into 3.2 ml of a mixture of 95% ethanol/triethylamine (9:1 ) at 80° C. to form a clear solution. The solution is cooled until a hazy suspension is obtained 5 mg (2.5%) of (+)-narwedine is added at 69° C. The solution is then cooled further to 40° C. and held there for 16 hours with stirring to form a white suspension. The suspension is then cooled to 25° C. and stirred for another 3 hours. The precipitate is collected by filtration and the cake washed with 1 ml of a solvent mixture of (9:1 ) 95% ethanol/triethylamine. The washed product is dried under vacuum at 25° C. for 30 minutes to yield 0.164 grams of white powder (84%) which is (+)-narwedine. {$[\alpha]_D^{25} = +418$}.

Example III: Resolution of (±)-Narwedine to (+)-Narwedine using (+)-Narwedine as Resolving Agent Repeating Example II using: 15mg (7.5%) of (+)-narwedine as the resolving agent, results in an 85% yield with a product having $[\alpha]_D^{25} = +412.9$.

Example IV: Reduction of (+)-Narwedine to (+)-Galanthamine 2 mmole (1N in tetrahydrofuran {THF}) of L-Selectride ® (lithium tri-sec-butylborohydride, Aldrich) is charged into 8 ml THF and cooled to −78° C. 1 mmole of (+)-narwedine in 50 ml THF is added dropwise over a period of 30 minutes. After addition, the solution is stirred at −78° C. for 2 hours and then warmed to 0° C. 0.4 ml of methanol is added and the solution is warmed to 25° C. and stirred for 15 minutes. Solvent is then evaporated under vacuum to dryness to obtain a syrup. The syrup is dissolved in 0.5 ml CHCl$_3$ and the solution is loaded into a SiO$_2$ 200–400 mesh, 6A, column. The column is eluted with a solvent mixture of CH$_2$Cl$_2$/CH$_3$OH 6:1 to obtain pure (+)-galanthamine.

Example V: Resolution of (±)-Narwedine to (−)-Narwedine using (+)-Galanthamine as Resolving Agent 10 grams of (±)-narwedine and 100mg (+)-galanthamine (1%) are placed in a flask having a reflux condenser. 160 ml of a solvent mixture of (9:1) 95% ethanol/triethylamine is added and the suspension is heated to 80° C., and stirred for 30 minutes until a clear colorless solution is formed. The temperature is reduced to 40° C. and held there with stirring for 24 hours to result in a white suspension. The temperature is further reduced to 25° C. and stirred for another 2 hours. The precipitate is collected by filtration and the cake rinsed with 50 ml of a solvent mixture of (9:1) 95% ethanol/triethylamine. The rinsed product is then dried under vacuum at 25° C. for 1 hour to obtain 7.62 grams of white powder(76.2% ), which is (−)-narwedine. {m.p. 192°–193° C.; $[\alpha]_D^{25}=-414.7$}

The mother liquor can be saved and recycled.

Example VI: Recycling mother liquor of Example V

The mother liquor of Example V is evaporated to dryness under vacuum to obtain a white solid, which is theoretically 2.4 grams of racemic narwedine and 100 mg of (+)-galanthamine. 38 ml of a solvent mixture of (9:1) 95% ethanol/triethylamine is added and the suspension is heated to 80° C. with stirring until a clear solution is formed. The solution is cooled to 40° C. and held there for 16 hours with stirring to obtain a white suspension. The suspension is then cooled to 25° C., and then stirred for 2 hours. The resulting precipitate is collected by filtration and the cake is rinsed with 12.5 ml of (9:1) 95% ethanol/triethylamine. The rinsed product is dried to give 1.4 grams of additional (−)-narwedine. $[\alpha]_D^{25}=-403.1$. The total yield from Examples V and VI is 90.2%

Example VII: Resolution of (±)-Narwedine to (−)-Narwedine using (−)-Narwedine as Resolving Agent 0.2 grams of (±)-narwedine is dissolved into 3.2 ml of a mixture of 95% ethanol/triethylamine (9:1 ) at 80° C. to form a clear solution. The solution is cooled until a hazy suspension is obtained. 5 mg (2.5%) of (−)-narwedine is added at 68° C. The solution is then cooled further to 40° C. and held there for 16 hours with stirring to form a white suspension. The suspension is then cooled to 25° C. and stirred for another 3 hours. The precipitate is collected by filtration and the cake washed with 1 ml of a solvent mixture of (9:1) 95% ethanol/triethylamine. The washed product is dried under vacuum at 25° C. for 30 minutes to yield 0.168 grams of white powder (84%) which is (−)-narwedine. {m.p. 192°–193° C.; $[\alpha]_D^{25}=-407.5$}.

Example VIII: Reduction of (−)-Narwedine to (−)-Galanthamine 2 mmole (1 N in tetrahydrofuran {THF}) of L-Selectride ® (lithium tri-sec-butylborohydride, Aldrich)is charged into 8 ml THF and cooled to −78° C. 1 mmole of (−)-narwedine in 50 ml THF is added dropwise over a period of 30 minutes. After addition, the solution is stirred at −78° C. for 2 hours and then warmed to 0° C. 0.4 ml of methanol is added and the solution is warmed to 25° C. and stirred for 15 minutes. Solvent is then evaporated under vacuum to dryness to obtain a syrup. The syrup is dissolved in 0.5 ml CHCl$_3$ and the solution is loaded into a SiO$_2$200–400 mesh, 6A, column. The column is eluted with a solvent mixture of CH$_2$Cl$_2$/CH$_3$OH 6:1 to obtain 286 mg of pure (−)-galanthamine (a yield of 99.5%). HPLC of the resultant mixture indicates there is no epigalanthamine or lycoramine present. {m.p. 128°–129° C.; $[\alpha]_D^{25}=-93.4$}. Natural (−)-galanthamine has a melting point of 126°–127° C. ($[\alpha]_D^{25}=-91.0$)

Examples IX–X

The procedures outlined in Examples I and V are repeated using the corresponding enantiomer of epigalanthamine in place of the galanthamine as the resolving agent. Similar results are obtained.

Examples XI–XII

The procedures set forth in Examples IV and VIII are repeated using the products obtained in Examples IX and X, as appropriate. Similar yields and purity are obtained. Epigalanthamine and lycoramine are not identified in the products.

Examples XIII–XIV

Example VIII Is repeated using the conditions set forth in Table I below with similar results as in Example VIII being achieved. Repeating Example IV with these conditions gives results similar to that achieved in Example IV. The conditions in Example VIII are repeated in the Table for comparison purposes.

TABLE I

| | EXAMPLE NO. | | |
|---|---|---|---|
| | VIII | XIII | XIV |
| REDUCING AGENT | LiB(sec-butyl)$_3$H | Ksec-butyl(iBu)$_2$AlH | NaBH$_4$/CeCl$_3$ |
| MOLES PER MOLE NARWEDINE | 1 | 2 | 0.5 |
| DISSOLVED IN | TETRAHYDROFURAN (THF) | TOLUENE | THF |
| COOLED TO | −78° C. | −90° C. | −60° C. |
| HOLD AT THIS FOR | 2 HOURS | 3 | 1.5 |
| WARM TO | 0° C. | 10° C. | −5° C. |
| SOLVENT TO ADD | CH$_3$OH | ETHANOL | EtOC(O)CH$_3$ |
| WARM TO | 25° C. | 25° C. | 25° C. |
| HOLD AT THIS FOR | 15 MIN | 30 MIN | 1 HOUR |
| DRY PRODUCT AND REDISSOLVED IN | CHCl$_3$ | CH$_2$Cl$_2$ | CHCl$_3$ |

Examples XV-XXI

Example VIII is repeated using the following reducing agents in place of the L-Selectride ® (lithium tri-sec-butylborohydride) to achieve similar results as seen with Example VIII.

| Example No. | Reducing Agent |
|---|---|
| XV | LS-Selectride ® (Li trisamylborohydride) |
| XVI | K-Selectride ® (K tri-sec-butylborohydride) |
| XVII | KS-Selectride ® (K trisamylborohydride) |
| XVIII | N-Selectride ® (Na tri-sec-butylborohydride |
| XIX | Na trisamylborohydride |
| XX | Na bis(2-methoxyethoxy)aluminum dihydride |
| XXI | Li sec-butyl(di-isobutyl) aluminum hydride |

Examples XXII–XXV

Example VIII is repeated using the following reducing agents in place of the L-Selectride ®. Results analogs to those achieved in Example VIII are obtained.

| Example No. | Reducing Agent |
|---|---|
| XXII | NaBH$_4$/CeCl$_3$ (1:1) |
| XXIII | NaBH$_4$/CeCl$_3$ (1:4) |
| XXIV | LiAlH$_4$/AlCl$_3$ (1:2) |
| XXV | LiAlH$_4$/AlCl$_3$ (1:1) |

Examples XXVI–XXIX

Examples I–VIII are repeated using the corresponding compounds wherein R$_2$ is acetyl (Example XXVI), ethyl (Example XXVII), or R$_3$ is acetyl (Example XXVIII) or both R$_2$ and R$_3$ are acetyl (Example XXIX). Similar results are obtained as in Examples I–VIII.

Examples XXX and XXXI

Example VIII is repeated using NaBH$_4$ alone (Example XXX) or LiAlH$_4$ (Example XXXI) as the reducing agent in accordance with the teachings of the Barton reference. The reaction product contains in excess of 35% epigalanthamine.

We claim:

1. A process for the manufacture of an enantiomer of galanthamine or an ester, ether, or amide thereof of formulae I or Ia

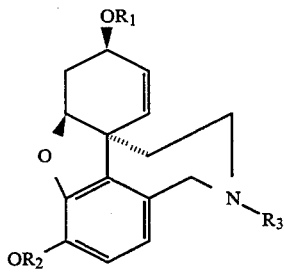

(I)

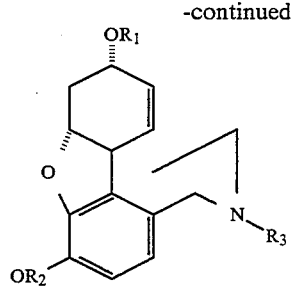

(Ia)

in which R$_1$ is selected from the group consisting of (a) hydrogen, (b) straight or branched C$_{1-7}$ alkanoyl, and (c) (R$_6$)(R$_7$)N—C(O)— in which each of R$_6$ and R$_7$ is selected from hydrogen or straight or branched C$_{1-7}$alkyl, or one of R$_6$ and R$_7$ may also be phenyl; R$_2$ selected from the group consisting of (a) hydrogen; (b) C$_{1-7}$ straight or branched alkyl; (c) straight or branched C$_{1-7}$ alkanoyl; and (d) (R$_6$)(R$_7$)N—C(O)— in which each of R$_6$ and R$_7$ is selected from hydrogen or straight or branched C$_{1-7}$alkyl, or one of R$_6$ and R$_7$ may also be phenyl; and R$_3$ is independently selected from the groups (a)–(c) defined for R$_2$ above;

comprising reacting the corresponding enantiomer of narwedine or an ester, ether, or amide thereof of formulae II or IIa

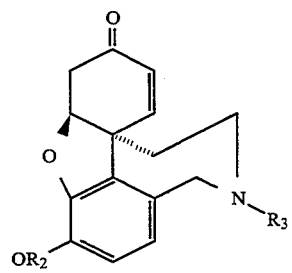

(II)

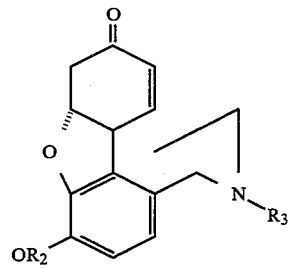

(IIa)

in which R$_2$ and R$_3$ are as defined above; with a reducing agent selected from the group consisting of compounds of formulas III–VII:

MB(R$_4$)$_p$H$_{4-p}$(III);

M$_q$Al(R$_4$)$_m$H$_{(3+q)-m}$(IV);

MAl(OR$_5$)$_n$H$_{4-n}$(V);

NaBH$_4$/CeCl$_3$(VI);

LiAlH$_4$/AlCl$_3$(VII); and mixtures thereof; in which m is 1, 2, or 3;

n is 1, 2, or 3;

p is 1, 2, or 3;
q is 0 or 1;
M is Li, Na, or K;
each $R_4$ is independently selected from the group consisting of straight and branched alkyl having 2–7 carbon atoms; and each $R_5$ is independently is selected from the group consisting of straight and branched alkyl having 2–7 carbon atoms and $R_8$—O—$R_9$— in which each $R_8$ is independently straight or branched alkyl of 1–3 carbon atoms, and each $R_9$ is independently 1,2-$C_{2-3}$alkylene or 1,3-propylene;
whereby said compound of formulae: I or Ia in which $R_1$ is hydrogen and $R_2$–$R_3$ are as defined above is produced without more than 20% production of epigalanthamine or an ester, ether, or amide thereof of formula VIII or VIIIa

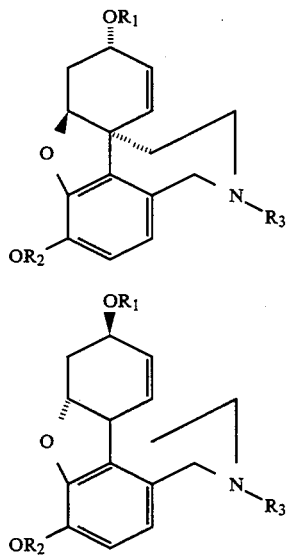

in which $R_1$–$R_3$ are as defined above.

2. The process of claim 1, wherein in said reducing agent of compounds of formula III, p is 3; and in compounds of formula IV, m is 2.

3. The process of claim 1 in which each $R_4$ is independently selected from ethyl, n-butyl, sec-butyl, iso-butyl, t-butyl, amyl, iso-amyl, sec-amyl, and t-amyl.

4. The process of claim 1 in which each $R_5$ is independently 2-methoxyethoxy or 2-ethoxyethoxy.

5. The process of claim 1 wherein said reducing agent is selected from compounds of formula III in which p is 3 and each $R_4$ is the same; compounds of formula IV in which q is 1, m is 3, and at least one $R_4$ is different from the others; and compounds of formula V in which n is 2 and each $R_5$ is the same; and mixtures thereof.

6. The process of claim 1 wherein said reducing agent is selected from the group consisting of bis(2-methoxyethoxy)aluminumhydride; lithium sec-butyl-bis-isobutylaluminumhydride; sodium borohydride/cesium chloride; lithium aluminumhydride/aluminum chloride; lithium tri-sec-butylborohydride; lithium triamylborohydride; potassium tri-sec-butylborohydride; potassium trisamylborohydride; sodium tri-sec-butylborohydride; and sodium trisamylborohydride.

7. The process of claim 1 further comprising preparing said enantiomer of formula II or IIa in economically high yield and purity from a racemic mixture of a compound of formula II and its corresponding enantiomer of formula IIa comprising dissolving said racemic mixture in a solvent/amine base mixture in which the solvent is selected from ethanol, isopropanol, toluene, acetone, acetonitrile, tetrahydrofuran, and ethyl acetate, and the amine base is selected from pyridine and $(R_{10})_3N$ in which each $R_{10}$ is independently $C_{2-4}$alkyl, said solvent and said amine base being in a ratio of from 1::9 to 15:1, at a temperature of from 20° C. to 80° C., then adding 0.1 to 2.0 % by weight (relative to the amount of racemate to be resolved) of a resolving agent selected from the group consisting of formula I, Ia, II, IIa, VIII, or VIIIa at a temperature of from 25° C. to 70° C.;

then reducing the temperature to 25° C. to 70° C. and held there for a period of 5–24 hours; and isolating the resulting crystals of the compound of either formula II or of formula IIa.

8. The process of claim 7 wherein said resolving agent is a first resolving agent and is a compound of formula Ia further comprising preparing said first resolving agent by dissolving a racemic mixture of a compound of formula II and its corresponding enantiomer of formula IIa in a solvent/amine base mixture in which the solvent is selected from ethanol, isopropanol, toluene, acetone, acetonitrile, tetrahydrofuran, and ethyl acetate, and the amine base is selected from pyridine and $(R_{10})_3N$ in which each $R_{10}$ is independently $C_{2-4}$alkyl, said solvent and said amine base being in a ratio of from 1:9 to 15:1, at a temperature of from 20° C. to 80° C., then adding 0.1 to 2.0% by weight (relative to the amount of racemate to be resolved for production of said first resolving agent) of a compound of formula I, IIa, or VIII at a temperature of from 25° C. to 70° C.; then reducing the temperature to 25° C. to 70° C. and holding the temperature there for a period of 5–24 hours;

isolating the resulting crystals of the compound of formula IIa; and reducing said resulting compound of formula with a reducing agent selected from compounds of formulas III–VII or mixtures thereof to yield a compound of formula Ia for use as the first resolving agent.

9. A process for the production of a substantially enantiomerically pure compound of formula II from a racemic mixture of said compound of formula II and its corresponding enantiomer of formula IIa wherein said formula II and IIa are:

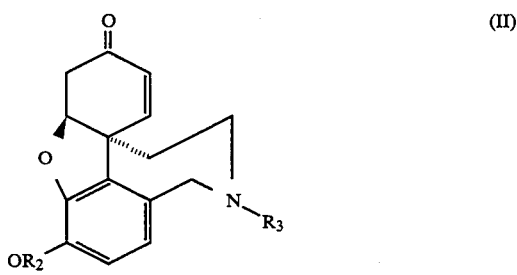

and

-continued

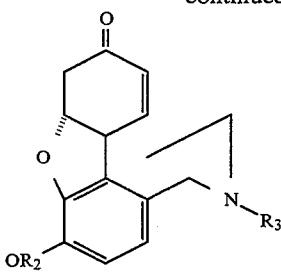
(IIa)

in which $R_2$ is selected from (a) hydrogen; (b) $C_{1-7}$ straight or branched alkyl; (c) straight or branched $C_{1-7}$ alkanoyl; and (d) $(R_6)(R_7)N—C(O)—$ in which each of $R_6$ and $R_7$ is selected from hydrogen or straight or branched $C_{1-7}$alkyl, or one of $R_6$ and $R_7$ may also be phenyl; and $R_3$ is independently selected flora the groups (a)—(c) defined for $R_2$ above; comprising dissolving a racemic mixture of a compound of formula II and its corresponding enantiomer of formula IIa in a solvent/amine base mixture in which the solvent is selected from ethanol, isopropanol, toluene, acetone, acetonitrile, tetrahydrofuran, and ethyl acetate, and the amine base is selected from pyridine and $(R_{10})_3N$ in which each $R_{10}$ is independently $C_{2-4}$alkyl, said solvent and said amine base being in a ratio of from 1:9 to 15:1, at a temperature of from 20° C. to 80° C., then adding 0.1 to 2.0% by weight (relative to the amount of racemate to be resolved) of a compound of formula Ia, or VIIIa in which formula Ia and VIIIa are:

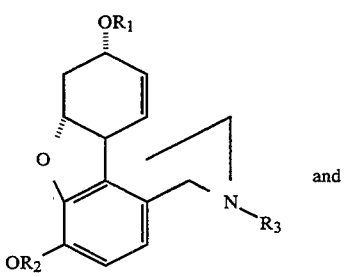
(Ia)

and

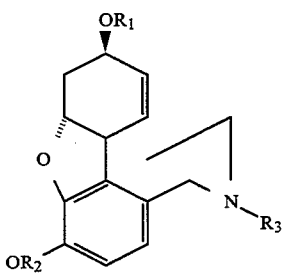
(VIIIa)

in which $R_1$ is selected from (a) hydrogen, (b) straight or branched $C_{1-7}$ alkanoyl, and (c) $(R_6)(R_7)N—C(O)—$ in which each of $R_6$ and $R_7$ is selected from hydrogen or straight or branched $C_{1-7}$alkyl, or one of $R_6$ and $R_7$ may also be phenyl; and $R_2$ and $R_3$ are as defined above; at a temperature of from 25° C. to 70° C.; then reducing the temperature to 25° C. to 70° C. and holding the temperature there for a period of 5-24 hours; and isolating the resulting crystals of the compound of formula II.

10. A process for the production of a substantially enantiomerically pure compound of formula IIa from a racemic mixture of said compound of formula II and its corresponding enantiomer of formula IIa wherein said formula II and IIa are:

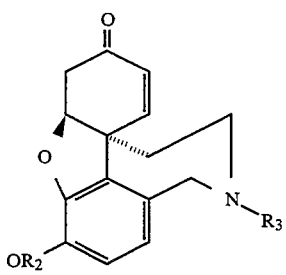
(II)

and

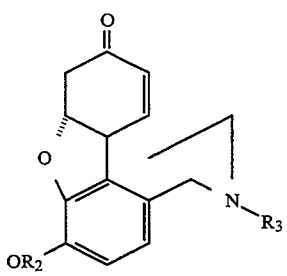
(IIa)

in which $R_2$ is selected from (a) hydrogen; (b) $C_{1-7}$ straight or branched alkyl; (c) straight or branched $C_{1-7}$alkanoyl; and (d) $(R_6)(R_7)N—C(O)—$ in which each of $R_6$ and $R_7$ is selected from hydrogen or straight or branched $C_{1-7}$alkyl, or one of $R_6$ and $R_7$ may also be phenyl; and $R_3$ is independently selected from the groups (a)–(c) defined for $R_2$ above; comprising dissolving a racemic mixture of a compound of formula II and its corresponding enantiomer of formula IIa in a solvent/amine base mixture in which the solvent is selected from ethanol, isopropanol, toluene, acetone, acetonitrile, tetrahydrofuran, and ethyl acetate, and the amine base is selected from pyridine and $(R_{10})_3N$ in which each $R_{10}$ is independently $C_{2-4}$alkyl, said solvent and said amine base being in a ratio of from 1:9 to 15:1, at a temperature of from 20° C. to 80° C., then adding 0.1 to 2.0 % by weight (relative to the amount of racemate to be resolved) of a compound of formula I, or VIII in which formula I and VIII are:

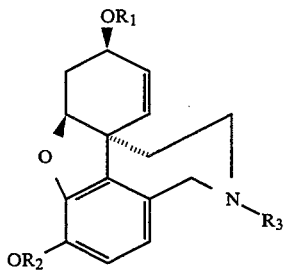
(I)

and

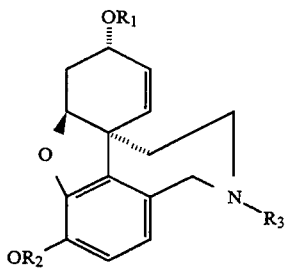

(VIII)

in which $R_1$ is selected from (a) hydrogen, (b) straight or branched $C_{1-7}$ alkanoyl, and (c) $(R_6)(R_7)N$—$C(O)$— in which each of $R_6$ and $R_7$ is selected from hydrogen or straight or branched $C_{1-7}$alkyl, or one of $R_6$ and $R_7$ may also be phenyl; and $R_2$ and $R_3$ are as defined above;

at a temperature of from 25° C. to 70° C.; then reducing the temperature to 25° C. to 70° C. and holding the temperature there for a period of 5-24 hours; and isolating the resulting crystals of the compound of formula IIa.

11. The process of claim 1 wherein the compound of formula I is (−)-galanthamine, the compound of formula Ia is (+)-galanthamine, the compound of formula II is (−)-narwedine, the compound of formula IIa is (+)-narwedine, the compound of formula VIII is (−)-epigalanthamine, and the compound of formula VIIIa is (+)-epigalanthamine.

12. The process of claim 9 wherein the compound of formula Ia is (+)-galanthamine, the compound of formula II is (−)-narwedine, the compound of formula IIa is (+)-narwedine, and the compound of formula VIIIa is (+)-epigalanthamine.

13. The process of claim 9 wherein the compound of formula I is (−)-galanthamine, the compound of formula II is (−)-narwedine, the compound of formula IIa is (+)-narwedine, and the compound of formula VIII is (−)-epigalanthamine.

14. A process for the production of a substantially enantiomerically pure compound of formula II or a substantially enantiomerically pure compound of formula IIa from a racemic mixture of said compound of formula II and its corresponding enantiomer of formula IIa wherein said formula II and IIa are:

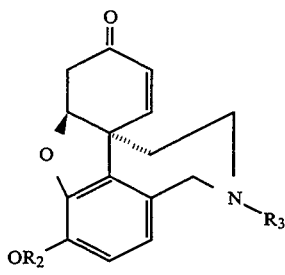

(II)

and

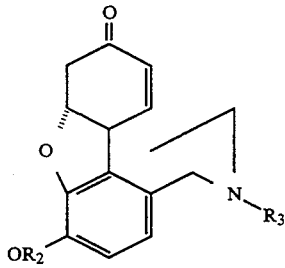

(IIa)

in which $R_2$ is selected from (a) hydrogen; (b) $C_{1-7}$ straight or branched alkyl; (c) straight or branched $C_{1-7}$ alkanoyl; and (d) $(R_6)(R_7)N$—$C(O)$— in which each of $R_6$ and $R_7$ is selected from hydrogen or straight or branched $C_{1-7}$alkyl, or one of $R_6$ and $R_7$ may also be phenyl; and $R_3$ is independently selected from the groups (a)–(c) defined for $R_2$ above; comprising dissolving a racemic mixture of a compound of formula II and its corresponding enantiomer of formula IIa in a solvent/amine base mixture in which the solvent is selected from ethanol, isopropanol, toluene, acetone, acetonitrile, tetrahydrofuran, and ethyl acetate, and the amine base is selected from pyridine and $(R_{10})_3N$ in which each $R_{10}$ is independently $C_{2-4}$alkyl, said solvent and said amine base being in a ratio of from 1:9 to 15:1, at a temperature of from 20° C. to 80° C., then adding 0.1 to 2.0% by weight (relative to the amount of racemate to be resolved) of a resolving agent which resolving agent is a substantially enantiomerically pure compound of formula II or of formula IIa other than the compound being resolved and which is the same optical rotation as the desired enantiomer of the racemate being resolved, at a temperature of from 25° C. to 70° C.; then reducing the temperature to 25° C. to 70° C. and held there for a period of 5-24 hours; and isolating the resulting crystals of the compound of formula II or IIa neither of which is the same compound as the resolving agent.

15. The process of claim 1 wherein $R_1$ is hydrogen or straight or branched $C_{1-7}$alkanoyl.

16. The process of claim 1 wherein $R_1$ is hydrogen.

17. The process of claim 9 wherein $R_1$ is hydrogen or straight or branched $C_{1-7}$alkanoyl.

18. The process of claim 9 wherein $R_1$ is hydrogen.

19. The process of claim 10 wherein $R_1$ is hydrogen or straight or branched $C_{1-7}$alkanoyl.

20. The process of claim 10 wherein $R_1$ is hydrogen.

* * * * *

UNITED STATES PATENT AND TRADEMARK OFFICE
CERTIFICATE OF CORRECTION

PATENT NO. : 5,428,159
DATED : Jun. 27, 1995
INVENTOR(S) : Wen-Chung Shieh, et al Page 1 of 23

It is certified that error appears in the above-indentified patent and that said Letters Patent is hereby corrected as shown below:

On page 3, column 3, lines 18 to 27 delete

"
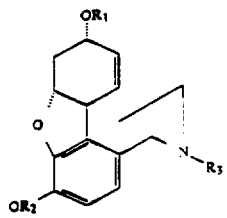
(Ia)
"

and insert

--
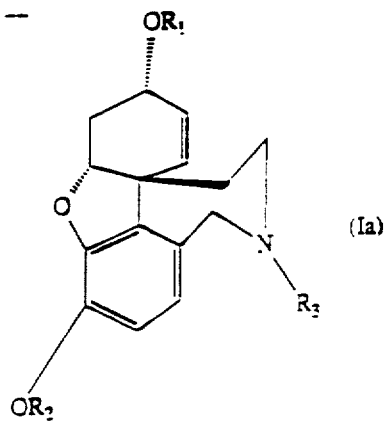
(Ia)
-- in lieu thereof.

UNITED STATES PATENT AND TRADEMARK OFFICE
CERTIFICATE OF CORRECTION

PATENT NO. : 5,428,159
DATED : Jun. 27, 1995
INVENTOR(S) : Wen-Chung Shieh, et al Page 2 of 23

It is certified that error appears in the above-indentified patent and that said Letters Patent is hereby corrected as shown below:

On page 3, column 3, lines 39 to 49 delete

"

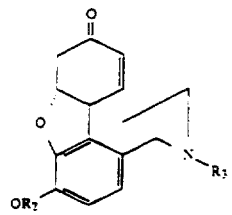

(IIa)

"

and insert

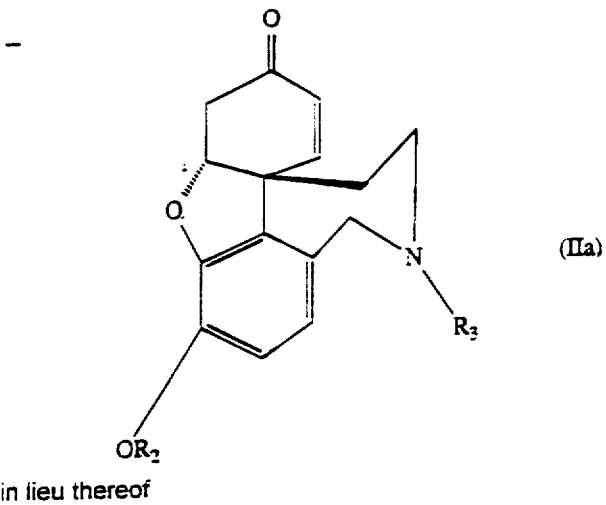

(IIa)

in lieu thereof

UNITED STATES PATENT AND TRADEMARK OFFICE
CERTIFICATE OF CORRECTION

PATENT NO. : 5,428,159

DATED : Jun. 27, 1995

INVENTOR(S) : Wen-Chung Shieh, et al

It is certified that error appears in the above-indentified patent and that said Letters Patent is hereby corrected as shown below:

On page 3, column 4, lines 57 to 68 delete

"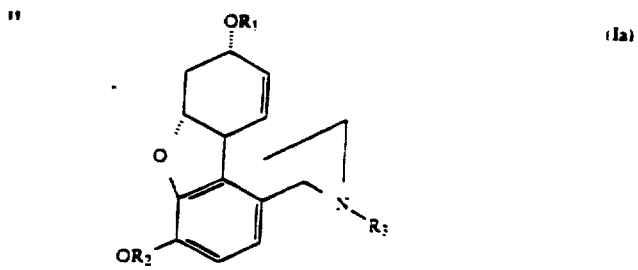 (Ia)

"

and insert

UNITED STATES PATENT AND TRADEMARK OFFICE
CERTIFICATE OF CORRECTION

PATENT NO. : 5,428,159
DATED : Jun. 27, 1995
INVENTOR(S) : Wen-Chung Shieh, et al It is certified that error appears in the above-indentified patent and that said Letters Patent is hereby corrected as shown below:

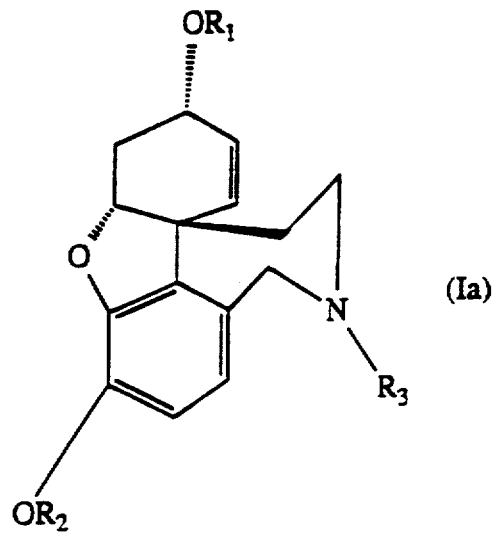

(Ia)

in lieu thereof

UNITED STATES PATENT AND TRADEMARK OFFICE
CERTIFICATE OF CORRECTION

PATENT NO. : 5,428,159
DATED : Jun. 27, 1995
INVENTOR(S) : Wen-Chung Shieh, et al It is certified that error appears in the above-indentified patent and that said Letters Patent is hereby corrected as shown below:

On page 4, column 5, lines 14 to 24 delete

"
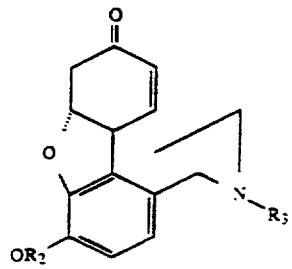
(IIa)
"

and insert

UNITED STATES PATENT AND TRADEMARK OFFICE
CERTIFICATE OF CORRECTION

PATENT NO. : 5,428,159
DATED : Jun. 27, 1995
INVENTOR(S) : Wen-Chung Shieh, et al It is certified that error appears in the above-indentified patent and that said Letters Patent is hereby corrected as shown below:

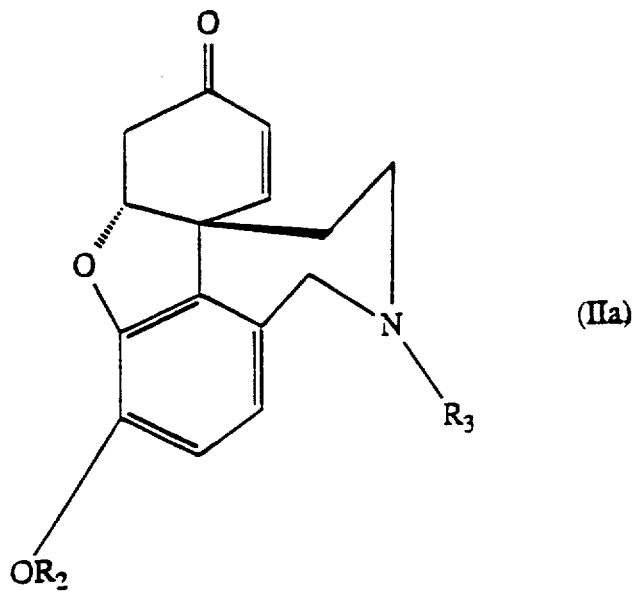
(IIa)

in lieu thereof

UNITED STATES PATENT AND TRADEMARK OFFICE
CERTIFICATE OF CORRECTION

PATENT NO. : 5,428,159                                Page 7 of 23
DATED : Jun. 27, 1995
INVENTOR(S) : Wen-Chung Shieh, et al It is certified that error appears in the above-indentified patent and that said Letters Patent is hereby corrected as shown below:

On page 4, column 6, lines 22 to 33 delete

"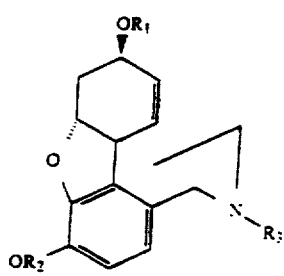 (VIIIa)
"

and insert

UNITED STATES PATENT AND TRADEMARK OFFICE
CERTIFICATE OF CORRECTION

PATENT NO. : 5,428,159
DATED : Jun. 27, 1995
INVENTOR(S) : Wen-Chung Shieh, et al Page 8 of 23

It is certified that error appears in the above-indentified patent and that said Letters Patent is hereby corrected as shown below:

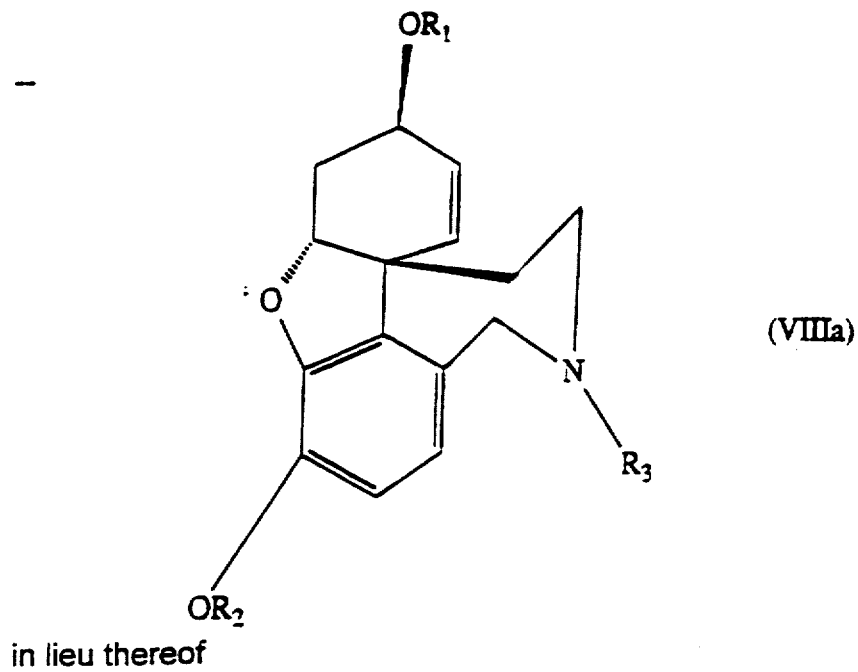

(VIIIa)

in lieu thereof

UNITED STATES PATENT AND TRADEMARK OFFICE
CERTIFICATE OF CORRECTION

PATENT NO. : 5,428,159  
DATED : Jun. 27, 1995  
INVENTOR(S) : Wen-Chung Shieh, et al It is certified that error appears in the above-indentified patent and that said Letters Patent is hereby corrected as shown below:

In claim 1
On page 7, column 12, lines 8 to 19 delete

"
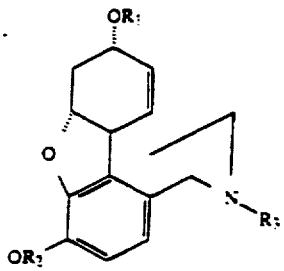
"

and insert

UNITED STATES PATENT AND TRADEMARK OFFICE
CERTIFICATE OF CORRECTION

PATENT NO. : 5,428,159                                       Page 10 of 23

DATED : Jun. 27, 1995

INVENTOR(S) : Wen-Chung Shieh, et al

It is certified that error appears in the above-indentified patent and that said Letters Patent is hereby corrected as shown below:

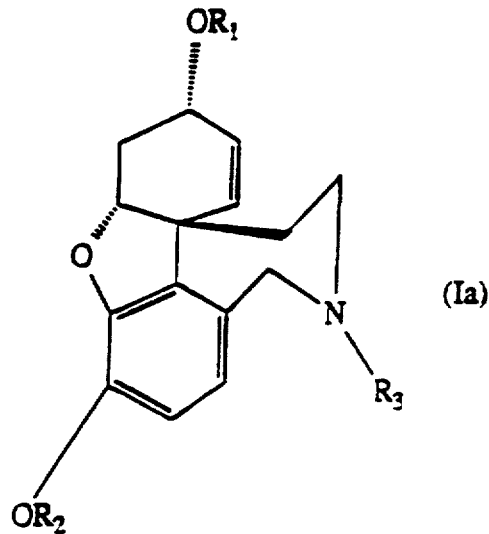

in lieu thereof

UNITED STATES PATENT AND TRADEMARK OFFICE
CERTIFICATE OF CORRECTION

PATENT NO. : 5,428,159
DATED : Jun. 27, 1995
INVENTOR(S) : Wen-Chung Shieh, et al It is certified that error appears in the above-indentified patent and that said Letters Patent is hereby corrected as shown below:

In claim 1
On page 7, column 12, lines 47 to 57 delete

"
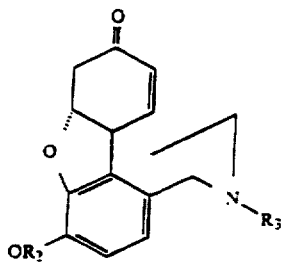
(IIa)
"

and insert

UNITED STATES PATENT AND TRADEMARK OFFICE
CERTIFICATE OF CORRECTION

PATENT NO. : 5,428,159  Page 12 of 23
DATED : Jun. 27, 1995
INVENTOR(S) : Wen-Chung Shieh, et al It is certified that error appears in the above-indentified patent and that said Letters Patent is hereby corrected as shown below:

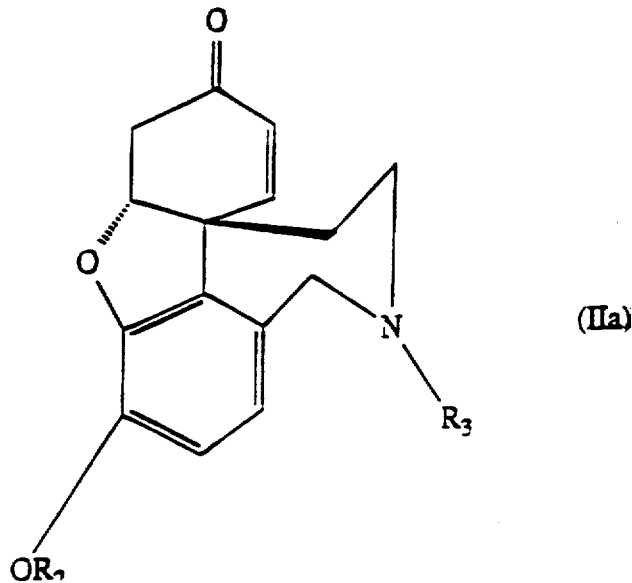

(IIa)

in lieu thereof

UNITED STATES PATENT AND TRADEMARK OFFICE
CERTIFICATE OF CORRECTION

PATENT NO. : 5,428,159                        Page 13 of 23

DATED : Jun. 27, 1995

INVENTOR(S) : Wen-Chung Shieh, et al

It is certified that error appears in the above-indentified patent and that said Letters Patent is hereby corrected as shown below:

In claim 1
On page 8, column 13, lines 28 to 39 delete

"
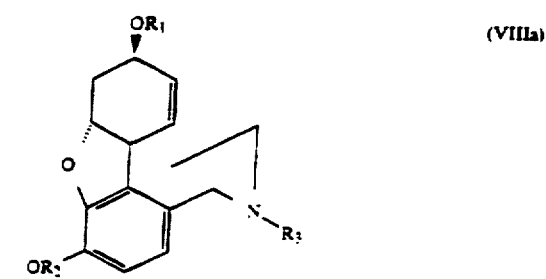
"

and insert

UNITED STATES PATENT AND TRADEMARK OFFICE
CERTIFICATE OF CORRECTION

PATENT NO. : 5,428,159
DATED : Jun. 27, 1995
INVENTOR(S) : Wen-Chung Shieh, et al It is certified that error appears in the above-indentified patent and that said Letters Patent is hereby corrected as shown below:

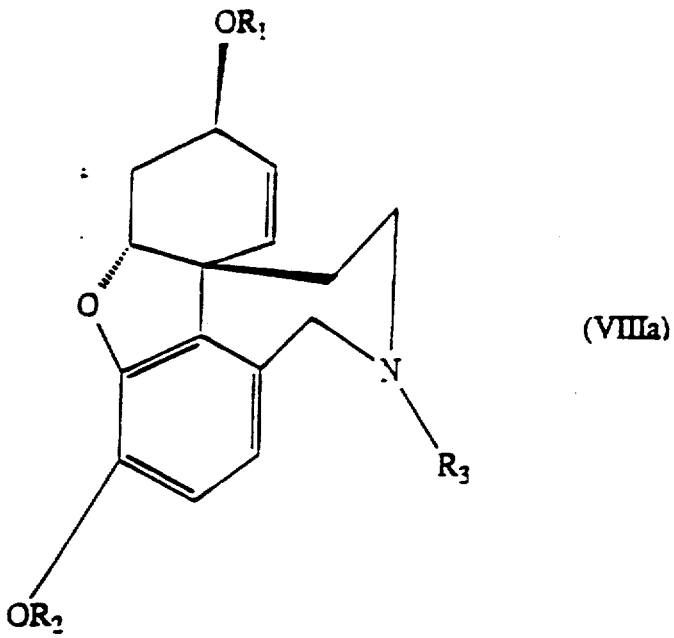

(VIIIa)

in lieu thereof

In claim 6, page 8, column 13, line 60 delete "triamylborohydride" and insert --trisamylborohydride--

UNITED STATES PATENT AND TRADEMARK OFFICE
CERTIFICATE OF CORRECTION

PATENT NO. : 5,428,159  Page 15 of 23
DATED : Jun. 27, 1995
INVENTOR(S) : Wen-Chung Shieh, et al It is certified that error appears in the above-indentified patent and that said Letters Patent is hereby corrected as shown below:

In claim 9
On page 9, column 15, lines 1 to 10 delete

"
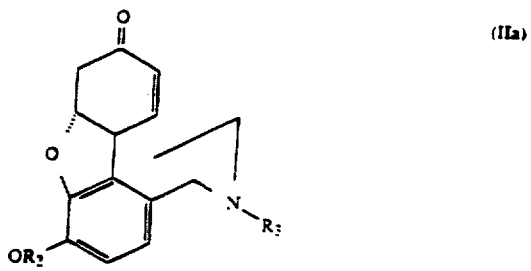
(IIa)
"

and insert

UNITED STATES PATENT AND TRADEMARK OFFICE
CERTIFICATE OF CORRECTION

PATENT NO. : 5,428,159
DATED : Jun. 27, 1995
INVENTOR(S) : Wen-Chung Shieh, et al It is certified that error appears in the above-indentified patent and that said Letters Patent is hereby corrected as shown below:

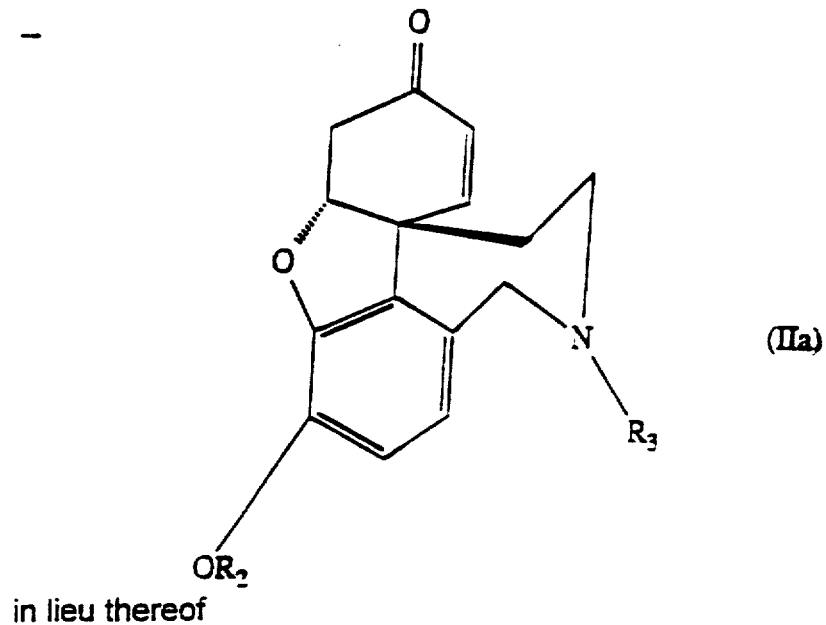

in lieu thereof

In claim 9, page 9, column 15, line 18 delete "flora" and insert —from—

UNITED STATES PATENT AND TRADEMARK OFFICE
CERTIFICATE OF CORRECTION

PATENT NO. : 5,428,159  Page 17 of 23
DATED : Jun. 27, 1995
INVENTOR(S) : Wen-Chung Shieh, et al It is certified that error appears in the above-indentified patent and that said Letters Patent is hereby corrected as shown below:

In claim 9
On page 9, column 15, lines 34 to 44 delete

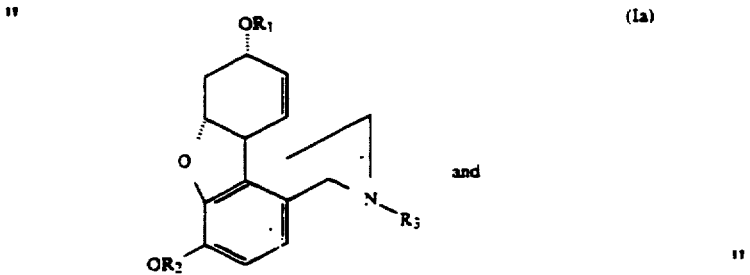

and insert

UNITED STATES PATENT AND TRADEMARK OFFICE
CERTIFICATE OF CORRECTION

PATENT NO. : 5,428,159  Page 18 of 23
DATED : Jun. 27, 1995
INVENTOR(S) : Wen-Chung Shieh, et al It is certified that error appears in the above-indentified patent and that said Letters Patent is hereby corrected as shown below:

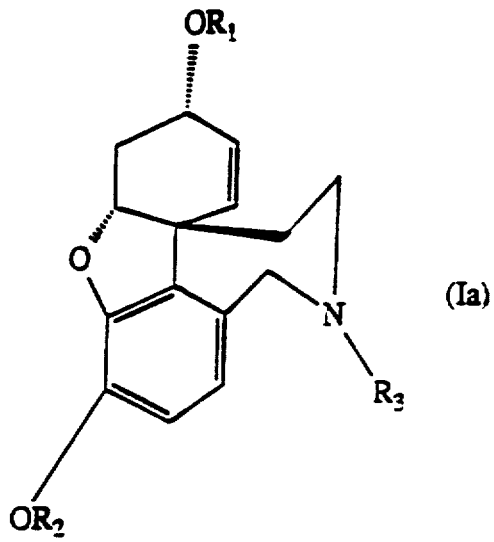

in lieu thereof

UNITED STATES PATENT AND TRADEMARK OFFICE
CERTIFICATE OF CORRECTION

PATENT NO. : 5,428,159

DATED : Jun. 27, 1995

INVENTOR(S) : Wen-Chung Shieh, et al

It is certified that error appears in the above-indentified patent and that said Letters Patent is hereby corrected as shown below:

In claim 9
On page 9, column 15, lines 45 to 55 delete

"
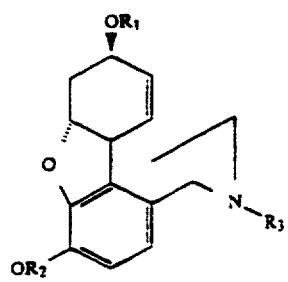
(VIIIa)
"

and insert

UNITED STATES PATENT AND TRADEMARK OFFICE
CERTIFICATE OF CORRECTION

PATENT NO. : 5,428,159
DATED : Jun. 27, 1995
INVENTOR(S) : Wen-Chung Shieh, et al It is certified that error appears in the above-indentified patent and that said Letters Patent is hereby corrected as shown below:

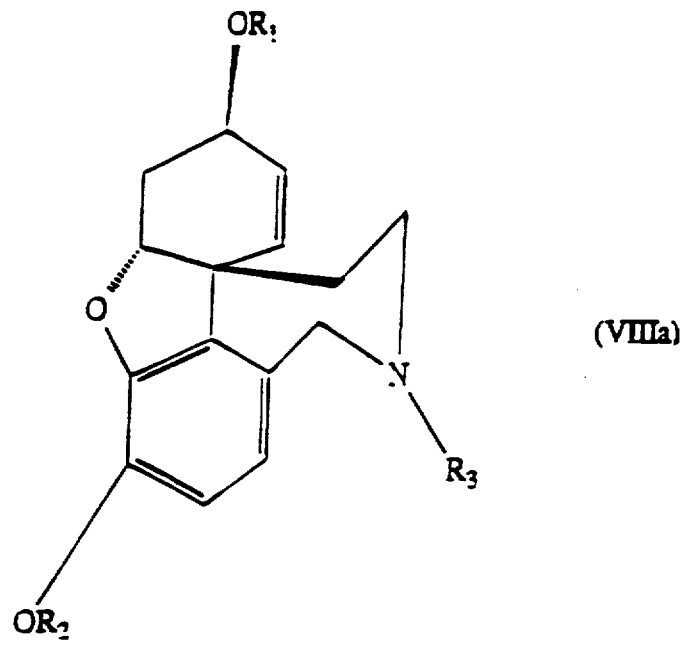

(VIIIa)

in lieu thereof

UNITED STATES PATENT AND TRADEMARK OFFICE
CERTIFICATE OF CORRECTION

PATENT NO. : 5,428,159
DATED : Jun. 27, 1995
INVENTOR(S) : Wen-Chung Shieh, et al It is certified that error appears in the above-indentified patent and that said Letters Patent is hereby corrected as shown below:

In claim 10, page 9, column 16, lines 19 to 29 delete

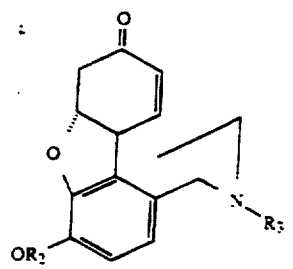

(IIa)

and insert

UNITED STATES PATENT AND TRADEMARK OFFICE
CERTIFICATE OF CORRECTION

PATENT NO. : 5,428,159

DATED : Jun. 27, 1995

INVENTOR(S) : Wen-Chung Shieh, et al

Page 22 of 23

It is certified that error appears in the above-indentified patent and that said Letters Patent is hereby corrected as shown below:

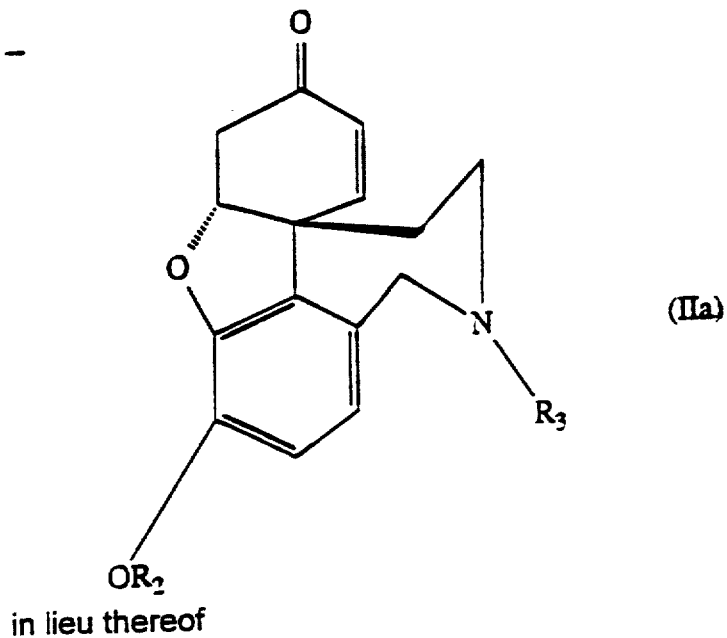

in lieu thereof

UNITED STATES PATENT AND TRADEMARK OFFICE
CERTIFICATE OF CORRECTION

PATENT NO. : 5,428,159
DATED : Jun. 27, 1995
INVENTOR(S) : Wen-Chung Shieh, et al It is certified that error appears in the above-indentified patent and that said Letters Patent is hereby corrected as shown below:

In claim 14, page 10, column 18, lines 15 to 25 delete

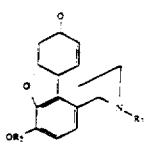

and insert

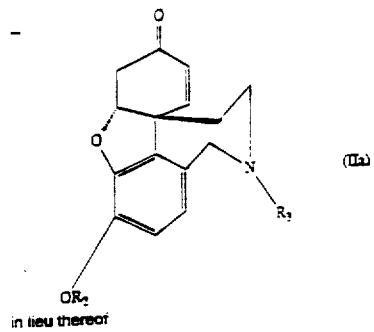

in lieu thereof

Signed and Sealed this

Seventh Day of November, 1995

Attest:

BRUCE LEHMAN

Attesting Officer

Commissioner of Patents and Trademarks